(12) United States Patent
Wang et al.

(10) Patent No.: US 9,140,714 B2
(45) Date of Patent: Sep. 22, 2015

(54) BIO-SENSING DEVICE

(71) Applicant: Wistron Corporation, New Taipei (TW)

(72) Inventors: Chia-Yuan Wang, New Taipei (TW);
Chi-Chan Chiang, New Taipei (TW);
Chih-Kuan Lin, New Taipei (TW);
Ting-Wen Liu, New Taipei (TW)

(73) Assignee: Wistron Corporation, New Taipei (TW)

( * ) Notice: Subject to any disclaimer, the term of this patent is extended or adjusted under 35 U.S.C. 154(b) by 103 days.

(21) Appl. No.: 14/024,647

(22) Filed: Sep. 12, 2013

(65) Prior Publication Data

US 2015/0010991 A1    Jan. 8, 2015

(30) Foreign Application Priority Data

Jul. 3, 2013 (TW) .............................. 102123855 A

(51) Int. Cl.
*G01N 35/00* (2006.01)
*B01L 3/00* (2006.01)

(52) U.S. Cl.
CPC .......... *G01N 35/0098* (2013.01); *B01L 3/5085* (2013.01); *B01L 2200/0668* (2013.01); *B01L 2300/0829* (2013.01)

(58) Field of Classification Search
CPC .......... B01L 3/5085; B01L 2300/0829; B01F 13/08; G01N 27/00; G01N 35/0098
See application file for complete search history.

(56) References Cited

U.S. PATENT DOCUMENTS

| | | | | |
|---|---|---|---|---|
| 3,356,346 | A * | 12/1967 | Landsberger | 366/274 |
| 5,567,326 | A * | 10/1996 | Ekenberg et al. | 210/695 |
| 6,176,609 | B1 * | 1/2001 | Cleveland et al. | 366/273 |
| 6,333,008 | B1 * | 12/2001 | Leistner et al. | 422/64 |
| 6,461,034 | B1 * | 10/2002 | Cleveland | 366/273 |
| 2002/0070173 | A1 * | 6/2002 | Otto et al. | 210/695 |
| 2002/0084225 | A1 * | 7/2002 | Hatch et al. | 210/695 |
| 2002/0098121 | A1 * | 7/2002 | Astle | 422/99 |
| 2003/0032205 | A1 * | 2/2003 | McFarland et al. | 436/518 |

* cited by examiner

*Primary Examiner* — Jill Warden
*Assistant Examiner* — Matthew Krcha
(74) *Attorney, Agent, or Firm* — Jianq Chyun IP Office

(57) ABSTRACT

A bio-sensing device includes a first platform, a second platform, at least one first magnetic element, and at least one second magnetic element. The first platform is configured to support a microplate. The microplate has a plurality of wells, each of which stores a reagent and a plurality of microbeads. The second platform is movably placed below the first platform. The first and the second magnetic elements are respectively located on the second platform. The first magnetic element moves along with the second platform to magnetically attract the microbeads in the wells, the second magnetic element moves along with the second platform to demagnetize the microbeads in the wells, and magnetism of the first magnetic element is opposite to magnetism of the second magnetic element.

5 Claims, 6 Drawing Sheets

BIO-SENSING DEVICE

CROSS-REFERENCE TO RELATED APPLICATION

This application claims the priority benefit of Taiwan application serial no. 102123855, filed on Jul. 3, 2013. The entirety of the above-mentioned patent application is hereby incorporated by reference herein and made a part of this specification.

BACKGROUND OF THE INVENTION

1. Field of the Invention

The invention relates to a bio-sensing device; more particularly, the invention relates to a bio-sensing device equipped with a demagnetization structure.

2. Description of Related Art

There are a number of existing cell separation technologies, such as a fluorescence activated cell separation (FACS) technology, a dielectrophoresis (DEP) cell separation technology, a micro-fabricated sieving separation technology, a magnetically activated cell separation (MACS) technology, and some optics-related and acoustics-related technologies.

Among these cell separation technologies, flow cytometry and the MACS technology are applied in most cases. Nevertheless, the frequently applied flow cytometry not only requires significant costs and a great number of samples but also has low bacterial disinfectant efficacy.

Different from flow cytometry, the MACS technology ensures that most target cells may be acquired within a relatively short period of time, and the separation principle of microbeads is based on the magnetic properties of the microbeads, i.e., the microbeads are magnetically attracted to the magnetic field and freely moved in a non-magnetic environment. Particularly, the microbeads are coated with specific antibodies which are attached to antigens of some desired cells via the antibody-antigen interaction. Thereby, the desired cells may be attached to the surfaces of the microbeads, such that the desired cells may be separated. Owing to the antibody-antigen interaction, the MACS technology is highly specific, simple, and cost-effective, and the sampling requirements for separation are low.

However, in the existing MACS technology, the microbeads with the weakened magnetic force may be gradually magnetized after being constantly controlled by the magnetic field. In the course of time, the microbeads in the wells tend to be gathered and attracted to one another even though the microbeads are not subject to any magnetic field; as a result, even in a non-magnetic environment, the microbeads can no longer move in a free manner.

SUMMARY OF THE INVENTION

The invention provides a bio-sensing device with a demagnetization structure, so as to demagnetize microbeads in wells.

In an embodiment of the invention, a bio-sensing device that includes a first platform, a second platform, at least one first magnetic element, and at least one second magnetic element is provided. The first platform is configured to support a microplate. The microplate has a plurality of wells, each of which stores a reagent and a plurality of microbeads. The second platform is movably placed below the first platform. The first magnetic element is located on the second platform. Besides, the first magnetic element moves along with the second platform to magnetically attract the microbeads in the wells. The second magnetic element is located on the second platform. Besides, the second magnetic element moves along with the second platform to demagnetize the microbeads in the wells. Magnetism of the at least one first magnetic element is opposite to magnetism of the at least one second magnetic element.

According to an embodiment of the invention, the number of the at least one first magnetic element in the bio-sensing device is plural, and the first magnetic elements are arranged in arrays on the second platform. Each of the first magnetic elements corresponds to at least one of the wells. The second platform approaches the first platform, such that the first magnetic elements magnetically attract the microbeads in the at least one of the wells.

According to an embodiment of the invention, an orthogonal projection of each of the first magnetic elements on the first platform is located between at least two adjacent wells of the wells.

According to an embodiment of the invention, the number of the at least one second magnetic element in the bio-sensing device is one, and the second magnetic element is located on the second platform and on a side of the first magnetic elements. When the first magnetic elements approach the wells, the second magnetic element moves away from the wells. When the second magnetic element approaches the wells together with the second platform, the first magnetic elements move away from the wells.

According to an embodiment of the invention, the first magnetic elements are arranged on the second platform along an axis. The second magnetic element is located on the axis and is away from the first magnetic elements.

According to an embodiment of the invention, the second platform ascends or descends relative to the first platform and moves along the axis.

According to an embodiment of the invention, the number of the at least one second magnetic element in the bio-sensing device is plural, and each of the second magnetic elements exclusively corresponds to one of the first magnetic elements. Each of the second magnetic elements and its corresponding first magnetic element are integrally formed.

According to an embodiment of the invention, the bio-sensing device further includes a reversal mechanism that is connected to the first magnetic elements, the second magnetic elements, and the second platform, so as to drive the first magnetic elements to face the wells or drive the second magnetic elements to face the wells.

According to an embodiment of the invention, the number of the at least one second magnetic element in the bio-sensing device is plural. The first magnetic elements are located on a first surface of the second platform, and the second magnetic elements are located on a second surface of the second platform. The first surface faces against the second surface. The second platform reverses relative to the first platform, such that the first surface of the second platform faces the first platform, or the second surface of the second platform faces the first platform.

According to an embodiment of the invention, the bio-sensing device further includes an injection device that is movably placed above the first platform, so as to draw the reagent from the wells or inject the reagent into the wells.

As discussed above, in an embodiment of the invention, the first and second magnetic elements are located below the wells, and the first magnetic elements serve to provide the magnetic field that attracts the microbeads. The second platform then moves relative to the first platform, and the second magnetic elements (whose magnetism is opposite to magnetism of the first magnetic elements) are configured to demagnetize the microbeads. Thereby, the microbeads in the wells are subject to the control of the magnetic field; notwithstanding the magnetic field, the microbeads are not equipped with the magnetic properties. As a result, the microbeads may be effectively functioned when the cell separation technology is applied.

In order to make the aforementioned and other features and advantages of the invention comprehensible, embodiments accompanied with figures are described in detail below.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the invention.

DETAILED DESCRIPTION OF DISCLOSED EMBODIMENTS

Figure 1:
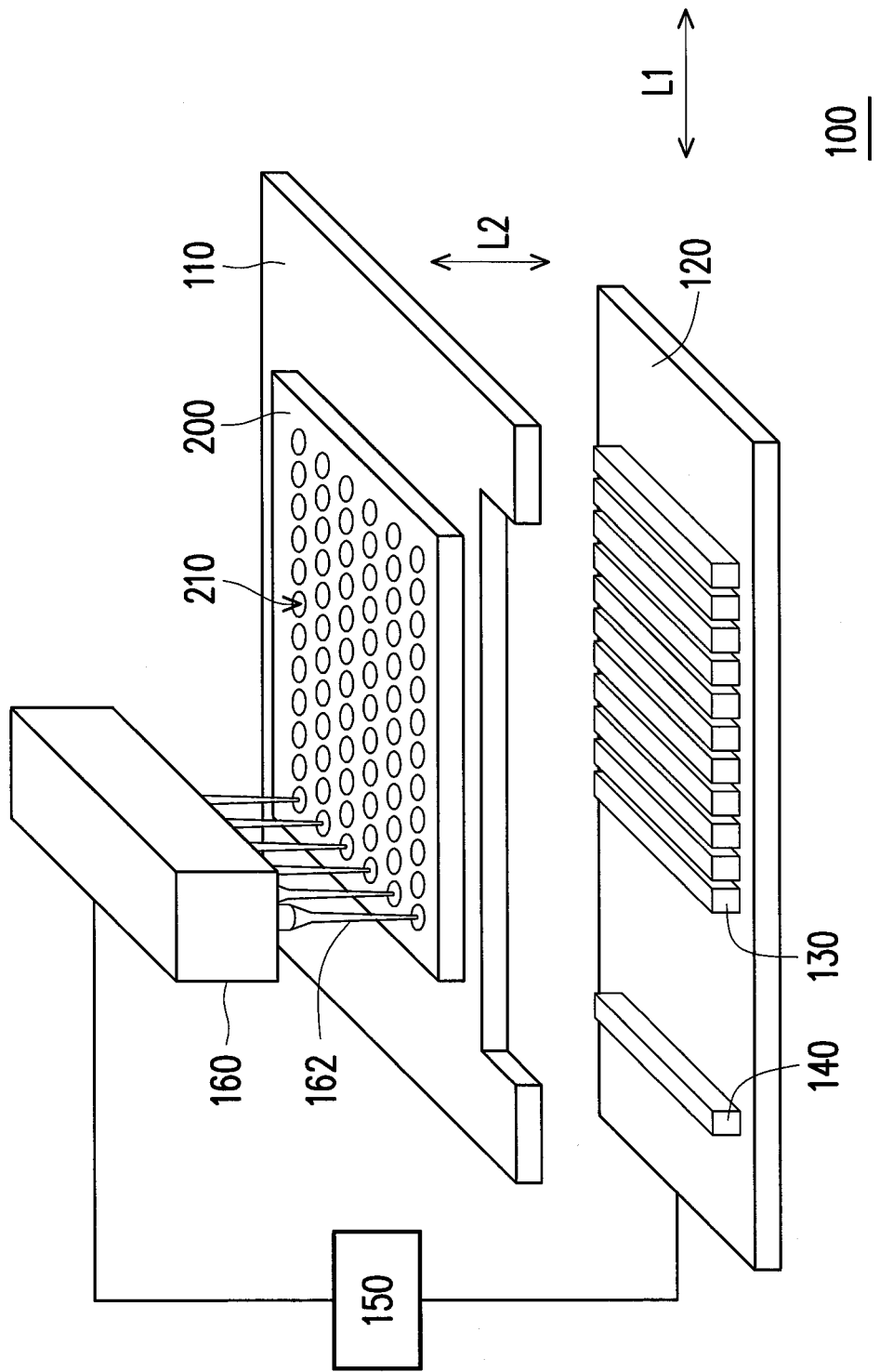
FIG. 1 is a schematic view illustrating a bio-sensing device according to an embodiment of the invention.
Figure 2:
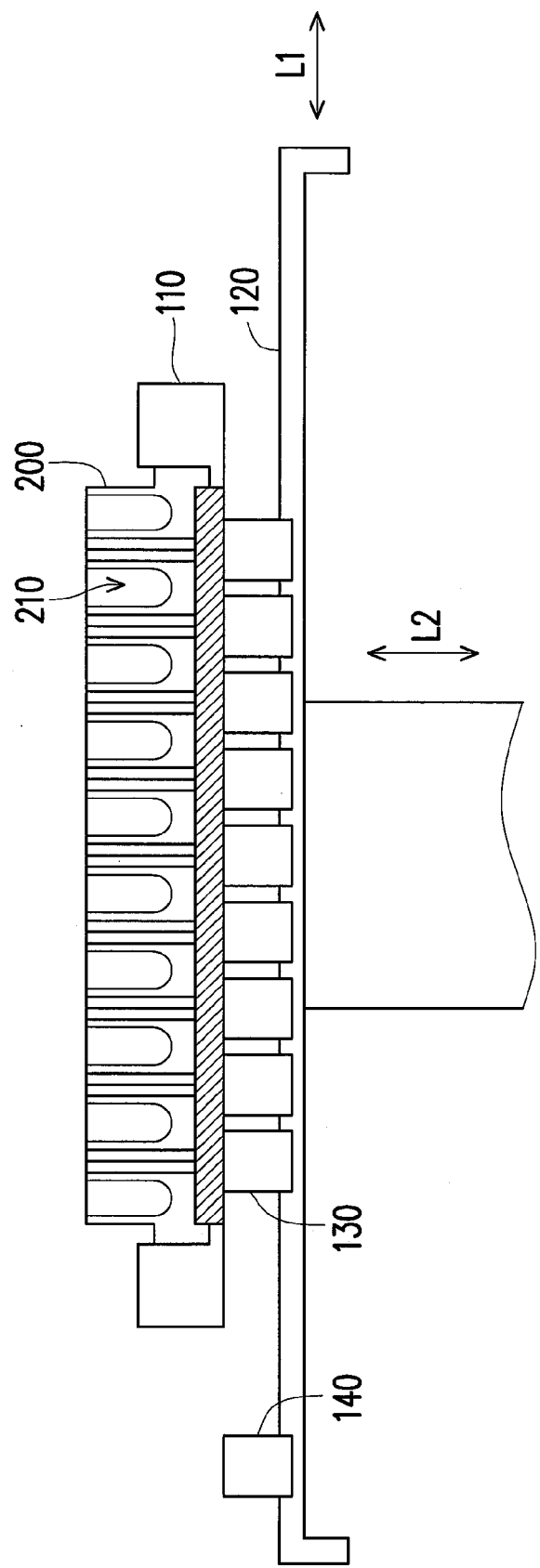
FIG. 2 is a partial side view illustrating the bio-sensing device depicted in FIG. 1.
Figure 3:
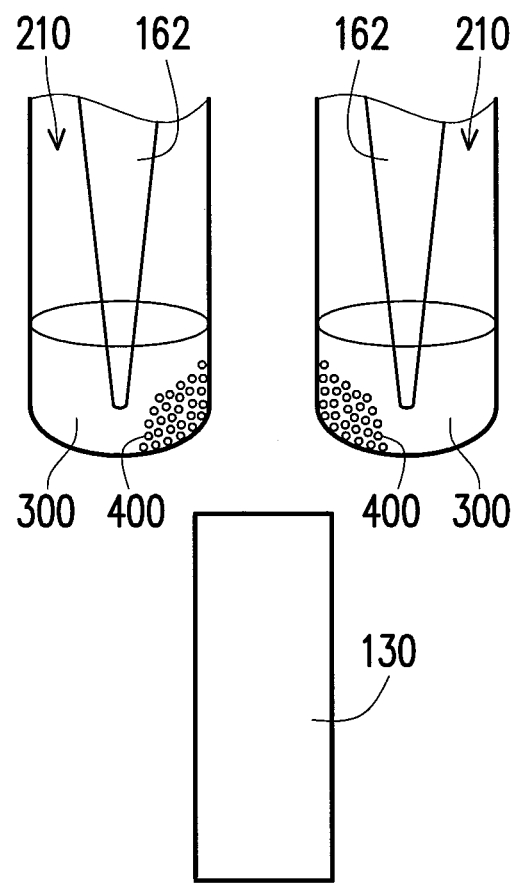
FIG. 3 is a partial enlarged view of FIG. 2.

FIG. 1 is a schematic view illustrating a bio-sensing device according to an embodiment of the invention. FIG. 2 is a partial side view illustrating the bio-sensing device depicted in FIG. 1. FIG. 3 is a partial enlarged view of FIG. 2. With reference to FIG. 1 to FIG. 3, in the present embodiment, the bio-sensing device 100 includes a first platform 110, a second platform 120, at least one first magnetic element 130, at least one second magnetic element 140, a control device 150, and an injection device 160. The first platform 110 is configured to support a microplate 200, the microplate 200 has a plurality of wells 210, and each of the wells 210 stores a reagent 300 and a plurality of microbeads 400 (shown in FIG. 3), so as to perform the separation processes.

In the present embodiment, the second platform 120 is located below the first platform 110, the first magnetic elements 130 are arranged in arrays on the second platform 120 along an axis L1, and the second magnetic element 140 is placed on the second platform 120 and on the axis L1. Note that the second magnetic element 140 is located on a side of the first magnetic elements 130 and away from the first magnetic elements 130, and magnetism of the first magnetic elements 130 is opposite to magnetism of the second magnetic element 140.

The control device 150 is electrically connected to the second platform 120 and the injection device 160, so as to drive the second platform 120 to move (i.e., slide and rotate) relative to the first platform 110. At the same time, the control device 150 drives the injection device 160 to move relative to the first platform 110 and inject the reagent 300 into the wells 210 or draw the reagent 300 from the wells 210 through the injection tube 162 of the injection device 160. In another embodiment that is not shown in the drawings, the control device 150 may be electrically connected to the first platform 110, so as to drive the first platform 110 to move relative to the second platform 120 and the injection device 160.

As shown in FIG. 2, the second platform 120 is adapted to be driven by the control device 150, such that the second platform 120 may be moved along the axis L1 and may ascend or descend along an axis L2 to approach or move away from the first platform 110. Thereby, when the first magnetic elements 130 move along with the second platform 120 and approach the first platform 110, the magnetic field of the first magnetic elements 130 affects the microbeads 400 in the wells 210. At this time, the second magnetic element 140 is away from the microplate 200, and thus the magnetism of the second magnetic element 140 does not pose any impact on the microbeads 400 in the wells 210.

As shown in FIG. 3, an orthogonal projection of each of the first magnetic elements 130 on the first platform 110 is located between at least two adjacent wells 210 but not limited thereto, and thus the microbeads 400 in the two wells 210 are gathered and magnetically attracted in a direction toward a corner of each well facing to the first magnetic elements 130. Thereby, the reagent 300 may be drawn from the wells 210 or injected into the wells 210 through the injection tube 162 without impact on the microbeads 400. By contrast, as shown in FIG. 2, the second magnetic element 140 is away from the fist magnetic elements 130. Therefore, when the orthogonal projection of each of the first magnetic elements 130 on the first platform 110 is located between at least two adjacent wells 210, an orthogonal projection of the second magnetic element 140 on the first platform 110 is located outside the microplate 200.

Due to the properties of the material (e.g., the weakened magnetic force) of the microbeads 400, if said movements (i.e., the second platform 120 approaches the first platform 110 and the first magnetic elements 130 magnetically attract the microbeads 400 in the wells 210) are repeated, the microbeads 400 are gradually magnetized by the first magnetic elements 130. Thereby, even though the second platform 120 does not approach the first platform 110, i.e., even though the magnetic field of the first magnetic elements 130 does not pose any impact on the microbeads 400, the microbeads 400 are affected by their magnetic properties and are thus gathered and attracted to one another. As such, the microbeads 400 in the wells 210 stay gathered, which is detrimental to the interaction between the microbeads 400 and the reagent 300.

In view of the above, the first magnetic elements 130 in the bio-sensing device 100 described in the present embodiment not only magnetically attract the microbeads 400 in the wells 210 but also demagnetize the microbeads 400, so as to prevent the microbeads 400 from being gathered and not being able to be separated.

Figure 4:
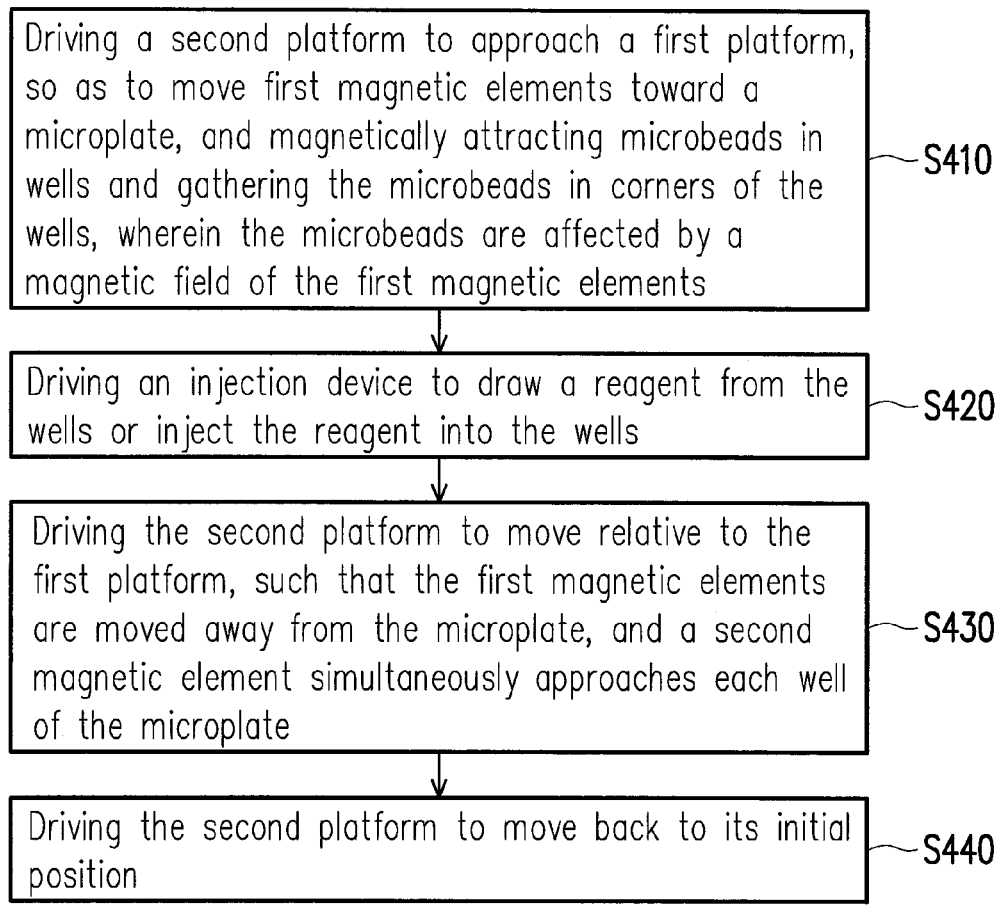
FIG. 4 is a flowchart illustrating a bio-sensing process according to an embodiment of the invention.

FIG. 4 is a flowchart illustrating a bio-sensing process according to an embodiment of the invention. In FIG. 4, the process of magnetically attracting the microbeads 400 and demagnetizing the microbeads 400 by means of the bio-sensing device 100 is explained. Please refer to FIG. 4 together with the device shown in FIG. 1 to FIG. 3. In step S410, the control device 150 drives the second platform 120 to approach the first platform 110, so as to move the first magnetic elements 130 toward the microplate 200. Besides, the microbeads 400 in the wells 210 are affected by the magnetic field of the first magnetic elements 130 and are thus gathered and magnetically attracted in the corners of the wells 210, so as to separate the reagent 300 from the microbeads 400. In step S420, the control device 150 further drives the injection device 160 to draw the reagent 300 from the wells 210 or inject the reagent 300 into the wells 210. In step S430, the control device 150 drives the second platform 120 to move relative to the first platform 110, such that the first magnetic elements 130 are moved away from the microplate 200, and the second magnetic element 140 approaches each well 210 of the microplate 200.

Specifically, as shown in FIG. 2, the second platform 120 described herein is moved along the axis L1 toward the right side of FIG. 2, and thus the moving second platform 120 drives the second magnetic element 140 (exemplarily shown in FIG. 2) to move from left to right and pass under each well 210. When the second magnetic element 140 passes under each well 210, the second magnetic element 140 is able to demagnetize the microbeads 400 in each of the wells 210 because the magnetism of the second magnetic element 140 is opposite to that of the first magnetic elements 130.

In step S440, the control device 150 drives the second platform 120 to move back to its initial position, such that the first magnetic elements 130 are moved together with the second platform 120 and are then moved back under the first platform 110 (i.e., the first magnetic elements 130 are moved back under the microplate 200). Thereby, the process of magnetically attracting the microbeads 400 in the wells 210 may be performed again.

Figure 5:
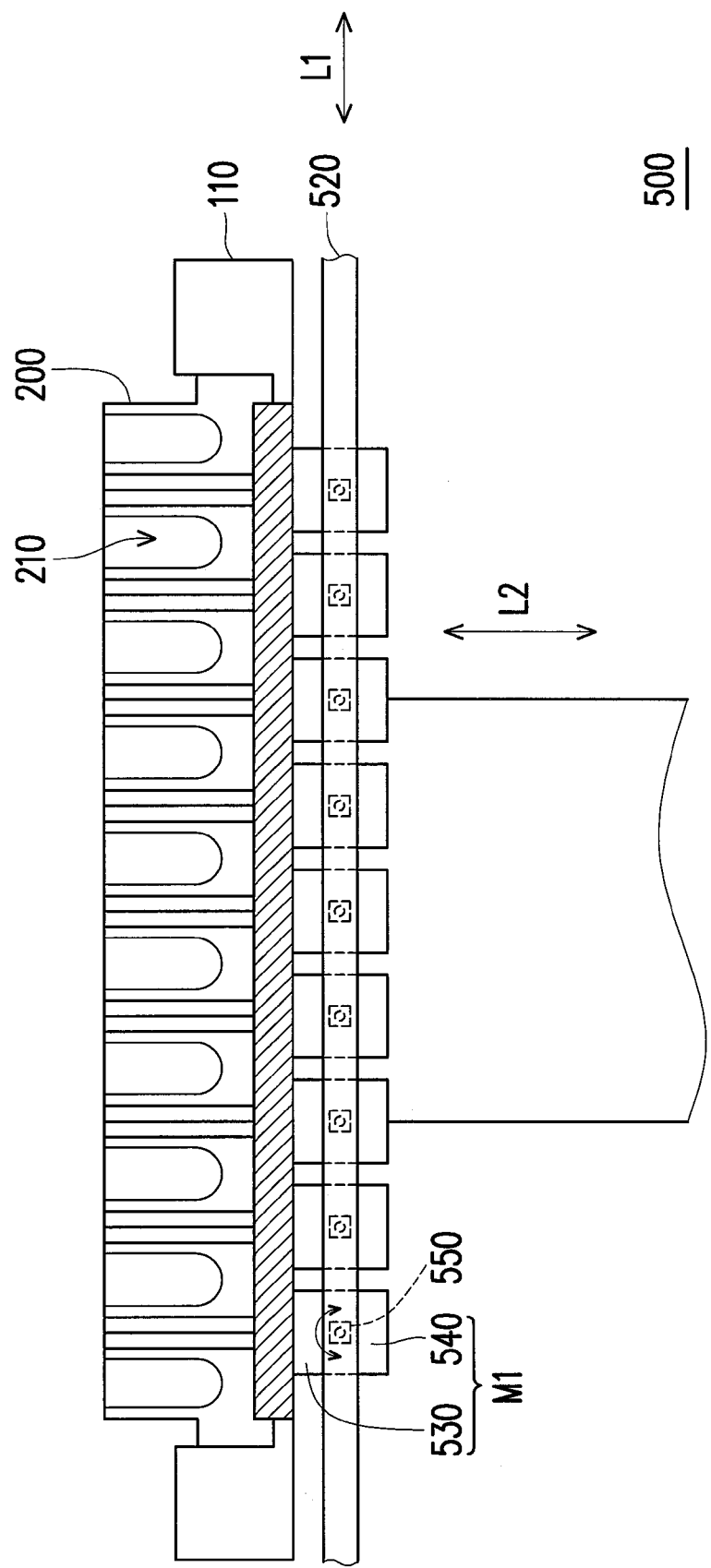
FIG. 5 is a partial side view illustrating a bio-sensing device according to another embodiment of the invention.

FIG. 5 is a partial side view illustrating a bio-sensing device according to another embodiment of the invention. With reference to FIG. 5, different from the bio-sensing device 100 described above, the bio-sensing device 500 includes a plurality of second magnetic elements 540, each of which corresponds to one of the first magnetic elements 530. In particular, each of the second magnetic elements 540 and its corresponding first magnetic element 530 are integrally formed, i.e., the corresponding first and second magnetic elements 530 and 540 are at different magnetic ends of the same magnetic device M1. The bio-sensing device 500 further includes a reversal mechanism 550 (e.g., a rotation axis or a hinge) that is connected to the first magnetic elements 530, the second magnetic elements 540, and the second platform 520. Besides, the reversal mechanism 550 and the second platform 520 are both subject to the control of the control device 150 (described in the previous embodiment). By means of the reversal mechanism 550, the control device 150 is able to rotate the magnetic device M1, such that the first magnetic elements 530 or the second magnetic elements 540 are driven to face the wells 210. That is, after the second platform 520 approaches the first platform 110, and the first magnetic elements 530 magnetically attract the microbeads 400 to perform the separation process, the magnetic device M1 may be directly driven by the reversal mechanism 550. Thereby, the second magnetic elements 540 can face the wells 210 and demagnetize the microbeads 400 in the wells 210. Certainly, the second magnetic elements 540 may also magnetically attract the microbeads 400 first, and the first magnetic elements 530 then serve to demagnetize the microbeads 400.

Figure 6:
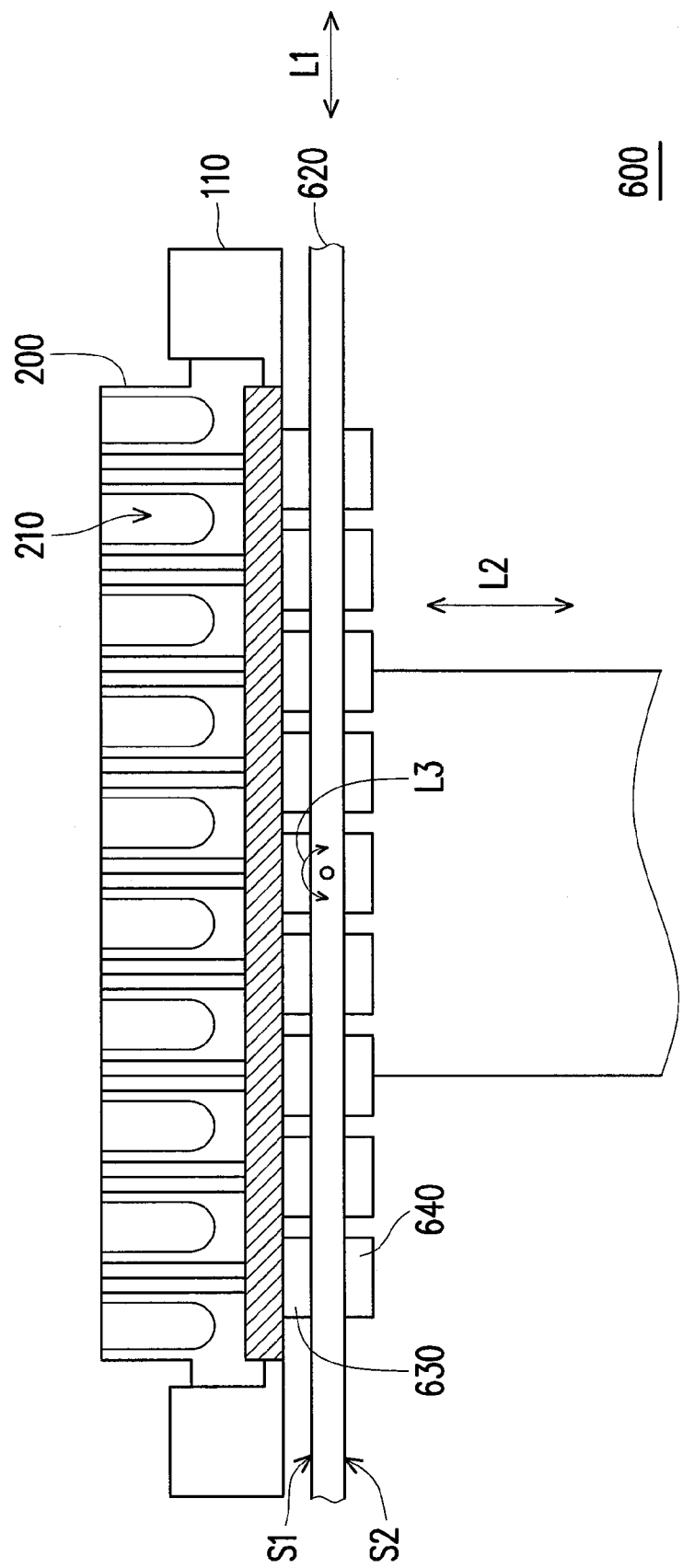
FIG. 6 is a partial side view illustrating a bio-sensing device according to yet another embodiment of the invention.

FIG. 6 is a partial side view illustrating a bio-sensing device according to yet another embodiment of the invention. With reference to FIG. 6, different from the bio-sensing device described above, the bio-sensing device 600 provided herein has the second platform 620 of which a first surface S1 and a second surface S2 are opposite to each other. The first magnetic elements 630 are located on the first surface S1 of the second platform 620, the second magnetic elements 640 are located on the second surface S2 of the second platform 620, and the second platform 620 reverses relative to the first platform 110 (along a rotation direction L3 shown in FIG. 6 after the platform 620 moving away from the first platform 110), such that the first surface S1 or the second surface S2 of the second platform 620 may face the microplate 200. The reversal movement of the second platform 620 allows the first magnetic elements 630 or the second magnetic elements 640 to face the wells 210, so as to magnetically attract or demagnetize the microbeads 400 in the wells 210.

To sum up, in the embodiments of the invention, the magnetism of the first magnetic elements on the second platform is opposite to the magnetism of the second magnetic elements on the second platform, such that the second platform may be driven to allow the first magnetic elements to magnetically attract the microbeads in the wells and allow the second magnetic elements to demagnetize the microbeads in the wells. As such, the bio-sensing device configured for conducting the separation technology is able to accomplish favorable separation effects in a constant manner, and the separation may not be affected by the magnetization resulting from the continuous magnetic attraction to the microbeads by the first magnetic elements with the same magnetism. Accordingly, the microbeads can move in an unrestrained manner if the microbeads are not subject to any magnetic field; moreover, the subsequent detection process may be performed easily and efficiently.

It will be apparent to those skilled in the art that various modifications and variations can be made to the structure of the disclosed embodiments without departing from the scope or spirit of the invention. In view of the foregoing, it is intended that the invention cover modifications and variations of this invention provided they fall within the scope of the following claims and their equivalents.

What is claimed is:

1. A bio-sensing device comprising:
    a first platform configured to support a microplate, the microplate having a plurality of wells, each of the wells storing a reagent and a plurality of microbeads;
    a second platform movably placed below the first platform;
    at least one first magnetic element located on the second platform, the at least one first magnetic element moving along with the second platform to magnetically attract the microbeads in the wells; and
    at least one second magnetic element located on the second platform, the at least one second magnetic element moving along with the second platform to demagnetize the microbeads in the wells, wherein magnetism of the at least one first magnetic element is opposite to magnetism of the at least one second magnetic element, wherein the number of the at least one first magnetic element is plural, the first magnetic elements are arranged in arrays on the second platform, each of the first magnetic elements corresponds to at least one of the wells, and the second platform approaches the first platform, such that the first magnetic elements magnetically attract the microbeads in the at least one of the wells, wherein the number of the at least one second magnetic element is plural, the first magnetic elements are located on a first surface of the second platform, the second magnetic elements are located on a second surface of the second platform, the first surface faces against the second surface, and the second platform reverses relative to the first platform between a first position and a second position, such that the first surface of the second platform faces the first platform in the first position, and the second surface of the second platform faces the first platform in the second position.

2. The bio-sensing device as recited in claim 1, wherein an orthogonal projection of each of the first magnetic elements on the first platform is located between at least two adjacent wells of the wells.

3. The bio-sensing device as recited in claim 1, wherein each of the second magnetic elements exclusively corresponds to one of the first magnetic elements, and each of the second magnetic elements and its corresponding first magnetic element are integrally formed.

4. The bio-sensing device as recited in claim 3, further comprising:
a reversal mechanism connected to the first magnetic elements, the second magnetic elements, and the second platform, so as to drive the first magnetic elements to face the wells or drive the second magnetic elements to face the wells.

5. The bio-sensing device as recited in claim 1, further comprising:
an injection device movably placed above the first platform, so as to draw the reagent from the wells or inject the reagent into the wells.

* * * * *